US008379953B2

(12) United States Patent
Bruder et al.

(10) Patent No.: US 8,379,953 B2
(45) Date of Patent: Feb. 19, 2013

(54) METHOD FOR CREATING COMPUTED TOMOGRAPHY RECORDINGS OF A PATIENT WITH METALLIC COMPONENTS

(75) Inventors: Herbert Bruder, Höchstadt (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 733 days.

(21) Appl. No.: 12/585,023

(22) Filed: Sep. 1, 2009

(65) Prior Publication Data

US 2010/0054569 A1 Mar. 4, 2010

(30) Foreign Application Priority Data

Sep. 2, 2008 (DE) .......................... 10 2008 045 449

(51) Int. Cl.
*G06K 9/00* (2006.01)
*A61B 6/00* (2006.01)
(52) U.S. Cl. ........................................... 382/131; 378/4
(58) Field of Classification Search .................. 382/131; 378/4, 207
See application file for complete search history.

(56) References Cited

U.S. PATENT DOCUMENTS

| 4,590,558 | A * | 5/1986 | Glover et al. ...................... 378/6 |
| 4,709,333 | A * | 11/1987 | Crawford ....................... 600/425 |
| 5,243,664 | A * | 9/1993 | Tuy ................................ 382/130 |
| 6,094,467 | A * | 7/2000 | Gayer et al. ....................... 378/4 |
| 6,426,988 | B2 * | 7/2002 | Yamada et al. .................... 378/4 |
| 6,721,387 | B1 | 4/2004 | Bechwati |
| 2005/0123089 | A1 * | 6/2005 | Man ................................ 378/4 |
| 2005/0123215 | A1 * | 6/2005 | Man .............................. 382/275 |
| 2006/0227928 | A1 * | 10/2006 | Timmer ............................. 378/4 |
| 2008/0031400 | A1 * | 2/2008 | Beaulieu et al. .................. 378/4 |
| 2009/0074278 | A1 * | 3/2009 | Beaulieu et al. .............. 382/131 |

FOREIGN PATENT DOCUMENTS

DE 10320233 A1 12/2004
WO WO 2006039809 A1 4/2006

OTHER PUBLICATIONS

1 Artifact reduction in truncated CT using Sinogram completion Proceedings of SPIE, Medical Imaging. vol. 5747, 2005, pp. 1605; Others; see IDS dated Jun. 10, 2009.

* cited by examiner

*Primary Examiner* — Alexander H Taningco
(74) *Attorney, Agent, or Firm* — Harness, Dickey & Pierce P.L.C.

(57) ABSTRACT

A method is disclosed for creating computed tomography recordings of a patient with metallic components. In at least one embodiment, the method includes scanning the patient by use of an x-ray tube detector system, with at least one sinogram being compiled; determining the detector signal data, which was attenuated by the metallic components in the patient; deleting the detector signal data, which was influenced by metallic components; determining the beam tracks in the sinogram at least of the volume elements, which are struck by beams which are attenuated by the metallic components and which cross the beam track of the deleted detector signal data in the sonogram; determining a minimal measurement value on each beam track respectively; adding together the minimal measurement values of the beam tracks to obtain the measurement points of the deleted detector signal data crossed by these beam tracks in the sonogram; and using this at least one sinogram determined in this manner to reconstruct computed tomography recordings of the patient without a metallic component, and displaying the reconstructed computed tomography recordings of the patient with metallic components.

23 Claims, 4 Drawing Sheets

$$p^{ImM}(\theta,l,q) = p^I(\theta,l,q) - p^M(\theta,l,q)$$

METHOD FOR CREATING COMPUTED TOMOGRAPHY RECORDINGS OF A PATIENT WITH METALLIC COMPONENTS

PRIORITY STATEMENT

The present application hereby claims priority under 35 U.S.C. §119 on German patent application number DE 10 2008 045 449.4 filed Sep. 2, 2008, the entire contents of which are hereby incorporated herein by reference.

FIELD

At least one embodiment of the invention generally relates to a method for creating computed tomography recordings of a patient with metallic components, the patient being scanned along a system axis of a CT system by at least one x-ray tube detector system and detector signal data from a plurality of projection angles being compiled in at least one sinogram and then being used to reconstruct computed tomography recordings.

BACKGROUND

A method for creating computed tomography recordings from detector signal data obtained by scanning a patient in a spiral or circular manner or from the projection data calculated therefrom is generally known. However if this detector signal data is determined from an examination object in the form of a patient containing a metallic structure, for example as a result of a previously inserted artificial joint made of metal, this metallic structure and the high level of absorption of the scanning x-ray radiation it produces generate image artifacts radiating from the structure.

SUMMARY

At least one embodiment of the invention establishes a method which allows such image artifacts produced by metallic structures to be suppressed to the greatest possible degree.

In at least one embodiment, the inventors have identified that it is possible to delete the detector signal data obtained by scanning the patient if it has been influenced by the metallic structure and to replace it with approximated detector signal data. If a computed tomography display is then reconstructed from detector signal data thus corrected, the radiating image artifacts caused by the metal also disappear. The data to be replaced can be at least accurately approximated, depending on its value, from the other detector signal data of all the voxels struck by a beam, which also intersects the metallic structure to be eliminated, during scanning.

It should be taken into account here that during scanning each of these voxels maps a beam track on the sinogram, said beam track being described by the beams from the focal point of the beam source by way of the voxel to the detector. One selection that proves very favorable here is the minimum value of all measured detector signals on a beam track. This value is transferred along the track to all the pixels influenced by the metal and deleted from the sinogram, with a number of beam tracks that strike a pixel resulting in a summing of the values. Since this method operates up to this point without standardization, the artificially generated pixel values should be adapted relative to the measured values of the sinogram.

In at least one embodiment, the inventors therefore propose an improvement of a method known per se for creating computed tomography recordings of a patient with metallic components, the method comprising:

scanning the patient along a system axis of a CT system by means of at least one x-ray tube detector system, with absorption data from a plurality of projection angles being compiled in at least one sinogram, and followed by reconstruction of computed tomography recordings.

In at least one embodiment, an inventive improvement is present in the following method steps:

determining the absorption data, which was attenuated by the metallic components in the patient, this forming at least one beam track in the at least one sinogram during scanning, deleting the absorption data, which was influenced by metallic components, from the at least one sinogram, determining the beam tracks in the at least one sinogram at least of the volume elements in the patient, which are struck by beams which are attenuated by the metallic components and which cross the beam track of the deleted absorption data in the at least one sinogram, determining a minimal measurement value on each determined beam track respectively, adding together all the minimal measurement values of all the beam tracks to obtain the measurement points of the deleted absorption data crossed by these beam tracks respectively in the at least one sinogram, using this at least one sinogram determined in this manner to reconstruct computed tomography recordings of the patient without the metallic component.

The method, of at least one embodiment, can advantageously be used not only in conjunction with a 2D reconstruction but also in conjunction with a volume reconstruction. Also with regard to the scan geometry it is possible to use both spiral scanning and circular scanning.

To determine the detector signal data, which was attenuated by the metallic components in the patient, it is possible to use for example a simple threshold value method in relation to the measured detector signal data.

More precise specification of the detector signal data attenuated by the metallic components in the patient is possible, if a back projection is performed with the projection data originally determined from the detector signal data and the metallic components are then segmented, with the data, which was attenuated by the metallic components in the patient, then being determined in the at least one sinogram by way of geometric calculations.

Alternatively it is also possible—if at least one embodiment of the present method is performed in the context of a multi-energy scan, for example in the context of a dual energy CT, or using energy resolving detectors—to perform material decomposition with the aid of at least two energy-specific items of image data to determine the metallic components, with the data, which was attenuated by the metallic components in the patient, then being determined in the at least one sinogram by way of geometric calculations. For the material decomposition method, see for example the German patent applications with the reference numbers 101 43 131 and 10 2005 049 586, the entire contents of which are hereby incorporated herein by reference.

The present method of at least one embodiment can be applied using sinograms based on both parallel projection and conical projection.

It is advantageous if the newly calculated sinogram data of the at least one sinogram is smoothed or standardized, it being possible for such smoothing to take place in relation to measurement data already present, to produce the gentlest transitions possible in the sinogram. Standardization can be under-taken for example by dividing the signal value in one pixel by the number of trajectories intersecting the pixel.

To perform a data reconciliation between the replaced measurement data and the originally measured data, a mean value can be formed in the boundary region and the corresponding data can be rescaled with the ratio of the mean values. For smoothing purposes, a weighted mean value can also be formed between the newly calculated sinogram data and the originally measured sinogram data and this can be used for reconstruction.

So that the computed tomography display is as realistic as possible, predetermined attenuation values can be input in the ultimately reconstructed computed tomography recordings in the previously determined region of the metallic components. Alternatively values can also be input in this region of the metallic components, which correspond to the predetermined attenuation values of metal or values can be taken from a reconstruction, which was performed without the correction measures described above.

In addition to at least one embodiment of the inventive method, at least one embodiment of the invention also includes a computer system for reconstructing, evaluating and displaying CT image data with a program storage unit containing computer programs, with at least one of the computer programs executing one of the methods described above during operation.

BRIEF DESCRIPTION OF THE DRAWINGS

The invention is described in more detail below based on an example embodiment with the aid of the figures, with only the features necessary for an understanding of the invention being shown.

The following reference characters are used here: 1: CT system; 2: first x-ray tube; 3: first detector; 4: second x-ray tube; 5: second detector; 6: gantry housing; 6.1: C arm/C-arm drive system; 7: patient; 8: movable patient support; 9: system axis; 10: control and computation unit; computer; 11: contrast agent applicator; 12: ECG line; 13: control line for contrast agent application; 14: measurement aperture in gantry housing; 15: metallic structure; 16: track of a metallic structure in the sinogram; 17: beam track in the sinogram; $Prg_1$-$Prg_n$: computer programs; S: beams; V: volume element.

In the figures:

Figure 1:
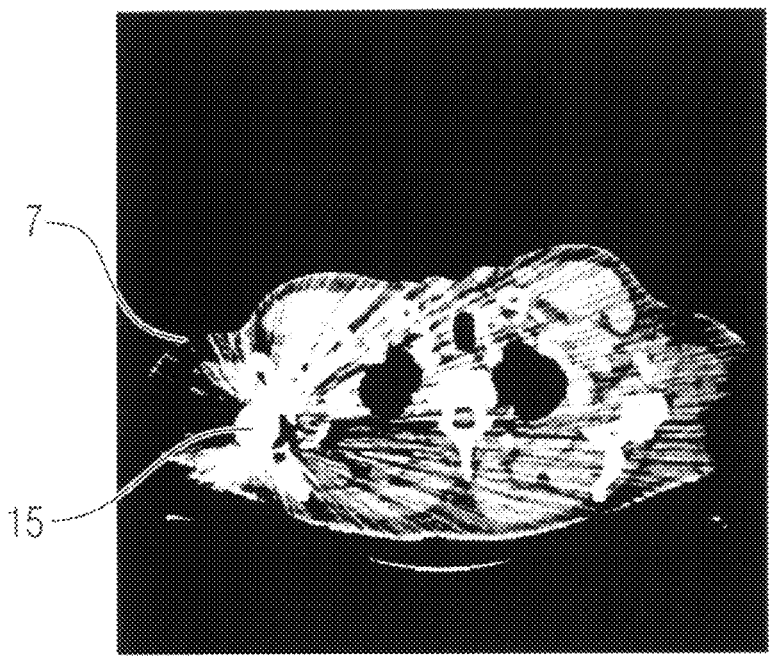
Figure 2:
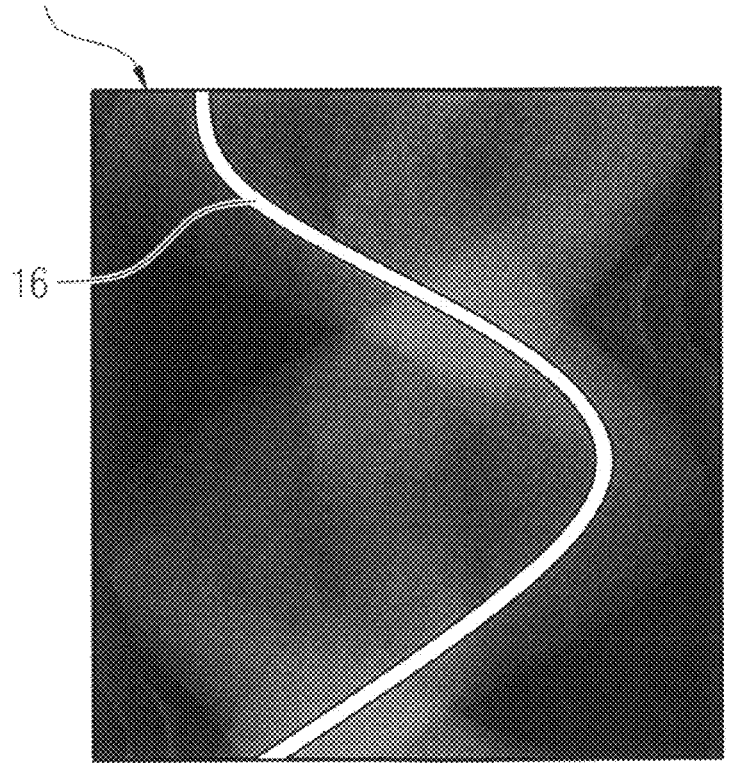
Figure 3:
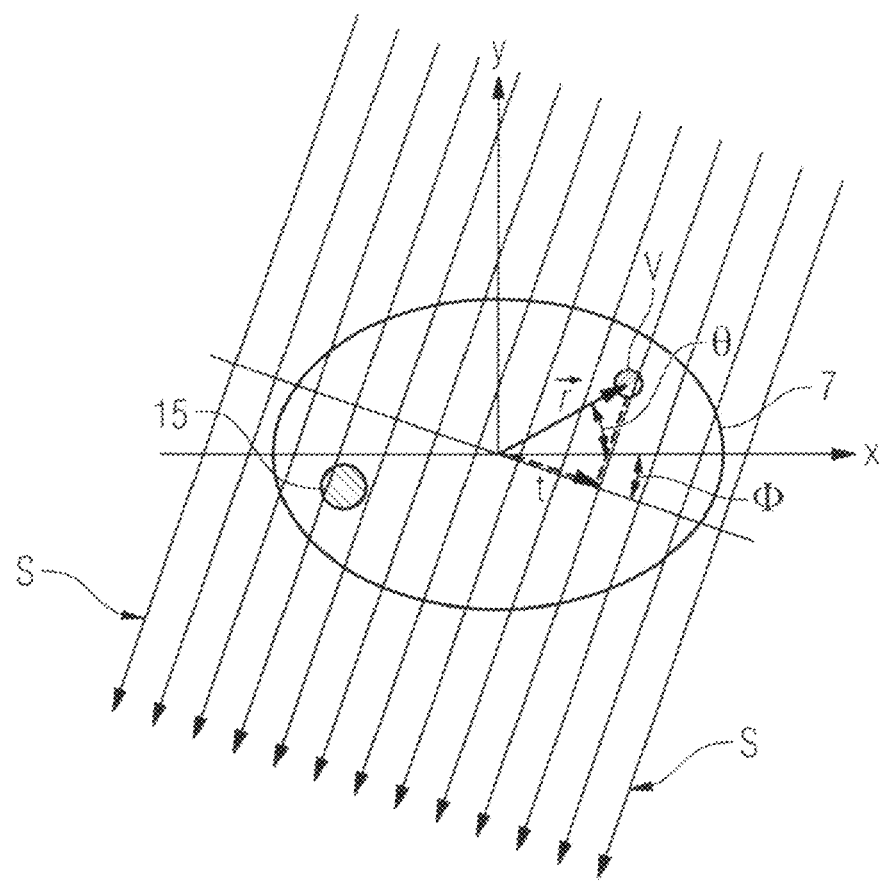
Figure 4:
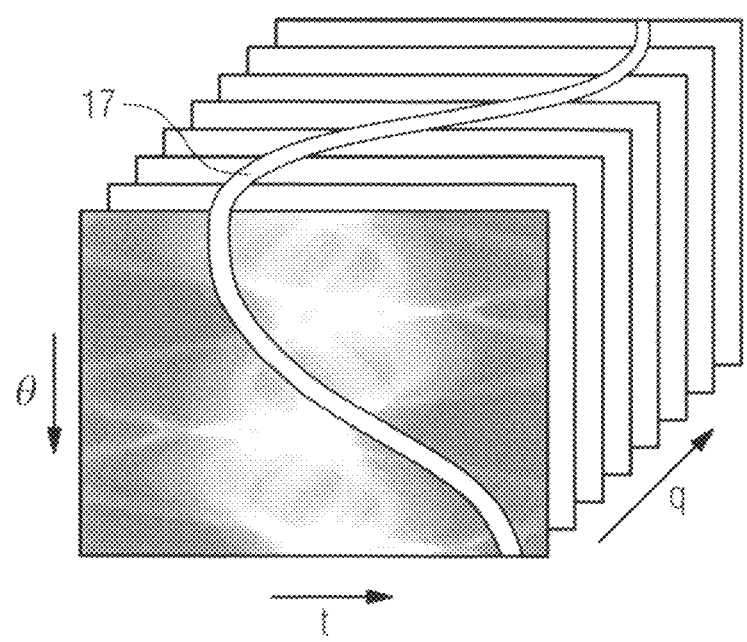
Figure 5:
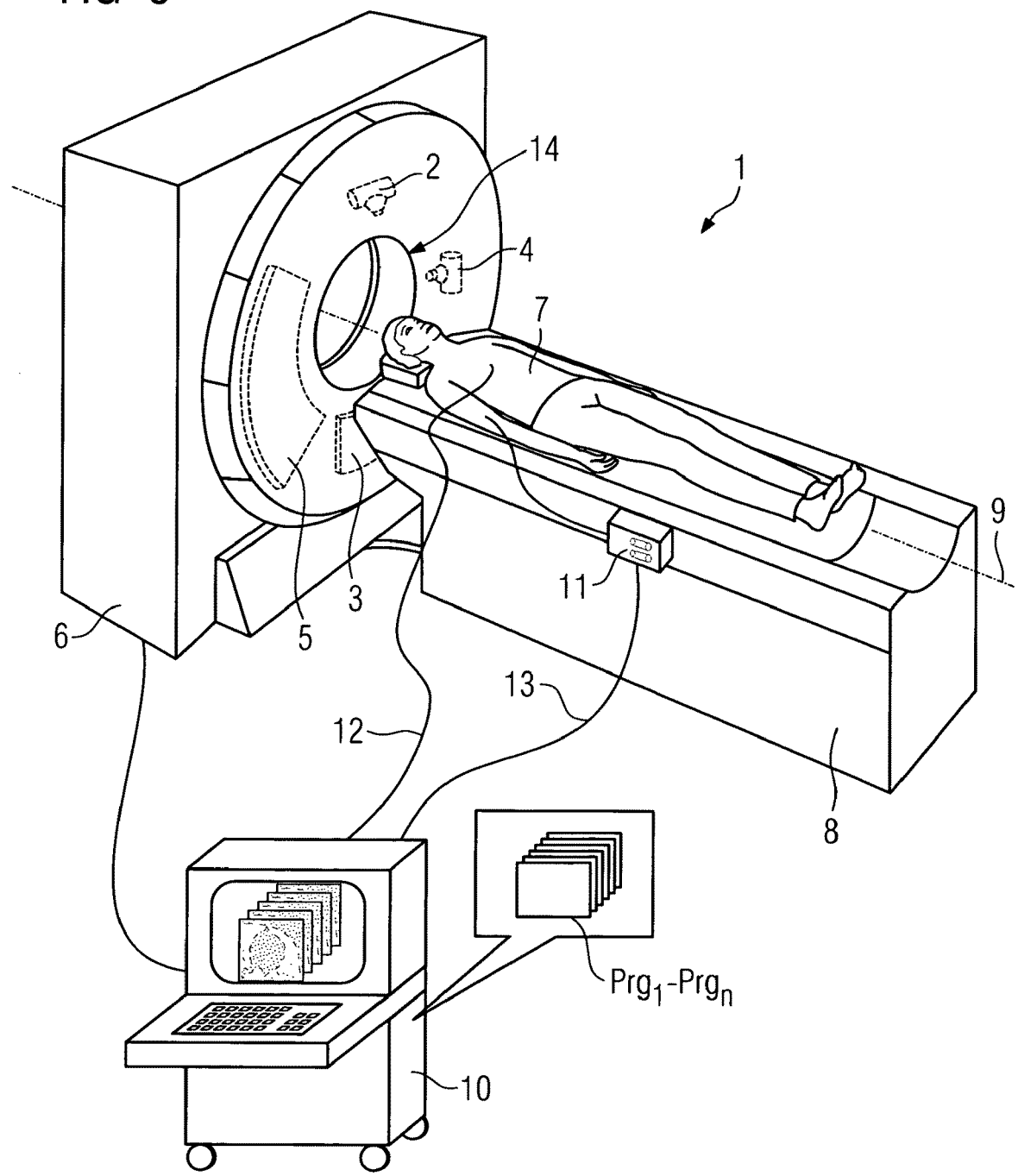
Figure 6:
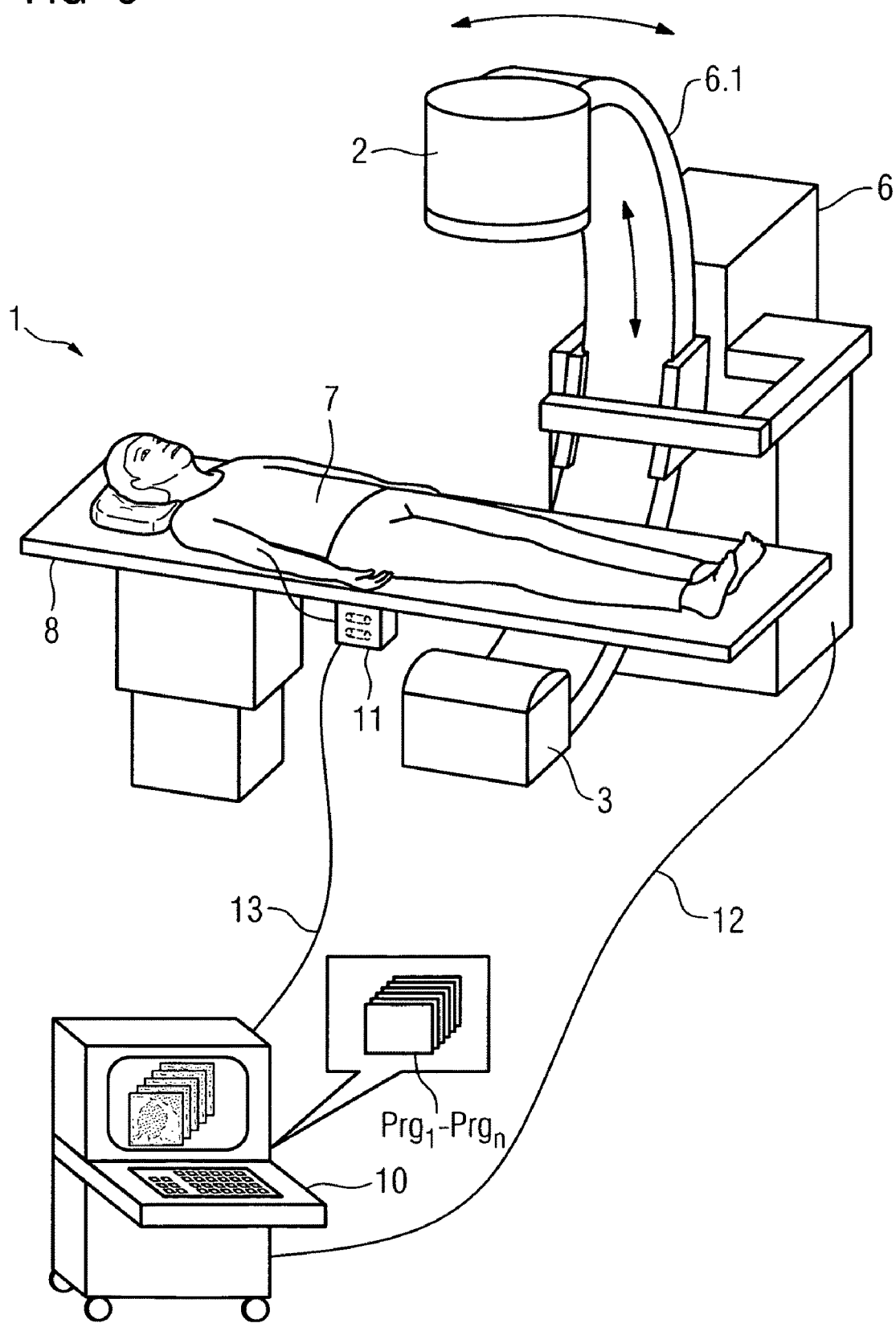

FIG. 1: shows a CT section of a patient with a metallic structure in the body and image artifacts radiating therefrom;

FIG. 2: shows a segment from a sinogram with deleted measurement data, which was influenced by metal;

FIG. 3: shows a diagram of the scan geometry;

FIG. 4: shows a 3D sinogram with a beam track of a volume element;

FIG. 5: shows a CT system;

FIG. 6: shows a C-arm system.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A method based on raw data is indicated below, which eliminates the metal artifacts to the greatest possible degree. The algorithm utilizes the basic concept of a sinogram decomposition, as described by way of example in R. Chityala, K. R. Hoffmann, S. Rudin, D. R. Bednarek, "Artifact reduction in truncated CT using Sinogram completion", Proceedings of SPIE, Medical Imaging, vol. 5747, 2005, pp. 1605, the entire contents of which are hereby incorporated herein by reference. In the example illustrated here the algorithm is applied to 3D CT spiral data, with metal artifacts now being corrected.

FIG. 1 shows a CT recording of a patient, in which a metal structure in the patient, in this instance a metallic femur neck prosthesis, produces significant image artifacts radiating from the metal structure and running in the direction of the scanning radiation. An embodiment of the inventive method for reducing such image artifacts in computed tomography recordings of a patient with metallic components, according to the underlying concept of the invention as described above, which is applied here specifically to 3D CT spiral data, can be broken down as follows:

1. Segmentation of the Metal Structures in a Reconstructed 3D Image Stack.

Such segmentation can take place in a manner known per se, for example by threshold value formation or other known methods, such as material decomposition, with the aid of a number of energy-specific CT recordings.

2. Reprojection of a Metal Structure Identified in Step 1 into the Raw Data Space, Preferably in Parallel Geometry.

This produces a sinogram $p^M(\theta,t,q)$, which is defined solely by the signals of the metal structure. $(\theta, t, q)$ here identify the parallel coordinates. The sinogram $p^M(\theta,t,q)$ thus identifies all the beams and measurement values which have experienced attenuation due to the metal structure.

3. Line by Line Parallel Rebinning of the CT Cone Beam Data.

Since the measurement data is generally present as cone beam projection data $p(\alpha,\beta,q)$, which in fan geometry is described by the projection angle $\alpha$, the fan position $\beta$ and the line number q, it can now be converted to parallel coordinates $(\theta, t, q)$ by means of the following equations:

$\theta = \alpha + \beta$ and $t = R_f \sin \beta$

The z position of the layer q of a parallel cone beam projection in parallel geometry is defined here in relation to the detector center as:

$$z = \left(q - \frac{N_q}{2}\right) \cdot \bar{S} + \eta; \quad (1)$$

$$\bar{S} = S \cdot \sqrt{1 - \left(\frac{t}{R_F}\right)^2},$$

$$\eta = z_{rot} \cdot \operatorname{asin}\left(\frac{t}{R_F}\right) / (2\pi)$$

where $R_f$ represents the distance between the focal point and the center of rotation, $z_{rot}$ the advance per revolution in spiral operation in the z direction and $N_q$ the number of detector lines. The projection values are then present as a three-dimensional parallel sinogram $p^r(\theta,t,q)$.

4. Subtraction of the Sinograms $p^r(\theta,t,q)$ and $p^M(\theta,t,q)$.

This also corresponds to an excision of all the attenuation values influenced by the metal structure in the sinogram. One line integral is assigned uniquely to each signal in the detector pixel. During summation of the minimal signals from different trajectories at the point of intersection difference objects are conceptually assumed, which each produce the signal trajectories. One signal trajectory is assigned uniquely to a pixel. It therefore makes sense to add minimal values together at the point of intersection. All the signals contributing to the total at the point of intersection then uniquely produce the line integral, which is assigned to the point of intersection.

This produces a sinogram $p^{tmM}(\theta,t,q)$, in which the metal region is blocked out. FIG. 2 shows a sub-region of such a sinogram $p^{tmM}(\theta,t,q)$. The black track 16 visible therein represents all the projection data, the beams of which were influenced by the metallic structure. The following then applies:

$p^{tmM}(\theta,t,q) = p^r(\theta,t,q) - p^M(\theta,t,q)$

5. Sinogram Completion by Means of Sinogram Decomposition.

A voxel V with the cylinder coordinates $(r,\Phi,z)$, according to the coordinates shown in FIG. 3, defines a beam track 17 in a parallel representation in a three-dimensional sinogram during spiral operation of a CT scan, as shown in FIG. 4.

FIG. 3 shows a section through a patient 7 with a metallic structure 15 in the Cartesian (x,y,z) coordinate system shown likewise in relation to the cylinder coordinates and parallel coordinates; the z-axis is not visibly perpendicular to the image plane. The parallel beams S correspond to the beams of a projection sorted in a parallel manner after a parallel rebinning. FIG. 4 shows a stack of a number of two-dimensional sinograms in the $\theta$,t plane, which in total correspond to a three-dimensional sinogram, with the sinogram planes corresponding in direction to the (detector) line number q. The beam track 17 here is also positioned above the sinograms, whereupon it should be pointed out that this diagram is simply schematic by nature.

The equation $$t(r, \theta, \Phi) = r \cdot \cos(\theta + \Phi) \quad (2)$$

$$y(r, \theta, \Phi) = r \cdot \sin(\theta + \Phi)$$

$$q(\theta, z) = \left| z - \frac{z_{rot} \cdot \left(\theta - \operatorname{asin}\left(\frac{t}{R_f}\right) / 2\pi\right)}{\tan(\vartheta_{cone}) \cdot R_f \cdot \sqrt{1 - \left(\frac{t}{R_f}\right)^2} + y} \right|$$

defines the beam track in the sinogram and/or the measurement values corresponding to this beam track. Here $\theta_{cone}$ represents the cone acceptance angle of the half detector and $R_f$ the distance between the focal point of the beam source used and the isocenter of the spiral motion of the beam source.

According to an embodiment of the invention all voxels outside the segmented metal region or preferably only the voxels outside the segmented metal region, which are intersected by beams, which also intersect the metal structure—for only these contain corresponding information—can now be considered. The completion of the excised data in the track 16 from FIG. 2 in the blocked out data region of $p^{tmM}(\theta,t,q)$ can now take place as follows:

$$\hat{p}(r, \Phi, z) = \min_{(t,\theta)} (p_\theta(t(r, \Phi, \theta), q(z, \theta)) \cdot I_\theta(t) \quad (3)$$

$$I_\theta(t) = \begin{Bmatrix} 1 \forall\ t = r \cdot \cos(\theta + \Phi) & q = q(r, \Phi, z, \theta) \\ 0 & sonst \end{Bmatrix} \text{(otherwise)}$$

A minimum found along the track of each voxel is therefore input into the blocked out data region. The basic concept here is that a δ object in the voxel (r,ø,z) in the sinogram would generate precisely this signal in the blocked out region.

If tracks overlap, the sum of the minimal signals found for the individual beam tracks is input in the relevant pixels of the sinogram. The data is thus added together. At the edges of the data region thus completed in the sinogram it may be necessary to adjust the signal level in the outer and inner region. This can be done for example by determining the signal levels in a track by mean value formation in a sub-region inside and outside and by eliminating discontinuities at the edge of the blocked out data region by corresponding scaling of the projection data. Also mixing the "minimum" signal and the actual signal at the edge of the blocked out data region within a track can help to eliminate discontinuities.

6. Backprojection of the Sinogram Data into a 3D Image Volume.

If a backprojection is now performed with the sinogram thus obtained, a display results without the interfering metal artifacts, as the corresponding information is no longer present in the sinograms.

7. Insertion of the Segmented Metal Signals into the 3D Image Volume.

The previously segmented region of the metallic structure in the CT display can then be replaced with artificial data, which corresponds to a mapping of this metal structure.

FIG. 5 shows a CT system 1, which is attached to the gantry in a gantry housing 6, a first tube/detector system, including an x-ray tube 2 and a detector 3 opposite it. A second tube/detector system, including an x-ray tube 4 and a detector 5 opposite it, is also shown as optional, it being possible to use this for faster scanning in the same energy range of the first tube/detector system, for example as part of a cardio examination or alternatively as part of a dual energy scan for a scan with different x-ray energy. The tube/detector systems in this example have an angular offset of 90° to one another in respect of their central beam. A patient 7 is present on the movable patient support 8, to whom a contrast agent can be administered with the aid of a contrast agent applicator 11, controlled by a control line 13 by way of the control and computation unit 10.

The patient 7 is moved along the system axis 9 through an aperture 14 in the gantry housing 6, while the tube/detector systems rotate and scan the patient 7. Scanning here can take place in the form of spiral scanning or in the form of sequential circular scanning. An ECG line 12 is also shown as optional in FIG. 5, likewise leading to the control and computation unit 10, so that gated scanning of the patient is possible. The control and computation unit 10 also controls the function of the CT system 1 as a whole, with the aid of computer programs $Prg_1$ to $Prg_n$. These computer programs $Prg_1$ to $Prg_n$ can also contain a computer program, which implements an embodiment of the inventive method directly at the CT system.

An embodiment of the inventive method can also be applied as part of CT examinations in conjunction with C-arm systems, as shown in FIG. 6. This C-arm system 1 has a tube/detector system, in which the x-ray tube 2 and the detector 3 opposite it are disposed on a C-arm 6.1 of a C-arm drive system 6. Corresponding rotation of the C-arm 6.1 allows the patient 7 on a patient support 8 to be scanned in a circular manner as with a CT system, through an angle of rotation of at least 180°, so that computed tomography displays can be reconstructed from the determined projection data. Contrast agent can be administered to the patient 7 with the aid of a contrast agent applicator 11 before or during the scan so that vessels are displayed more clearly.

The C-arm drive system 6 is controlled by a control and computation unit 10 by way of a control and data line 12. The control and computation unit 10 can also be used to trigger the contrast agent applicator 11 by way of a control line 13. In addition to the control programs, the programs $Prg_1$-$Prg_n$ of the control and computation unit 10 also contain programs for evaluating received data from the detector 3 and programs for reconstructing and displaying the CT image data, including an embodiment of the inventive correction method.

It should however be noted that an embodiment of the inventive method can also be executed in conjunction with standalone computation systems, once these computation systems receive at least projection data from a CT system or C-arm system.

It is evident that the above-mentioned features of the invention can be used not only in the respectively indicated combination but also in other combinations or alone, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating computed tomography recordings of a patient with metallic components, the method comprising:
    scanning the patient along a system axis of a CT system by use of at least one x-ray tube detector system, with detector signal data from a plurality of projection angles being compiled in at least one sinogram;
    determining the detector signal data, attenuated by the metallic components, represented by metallic volume elements in the patient, which form individual beam tracks in the at least one sinogram;
    deleting the detector signal data, attenuated by the metallic volume elements, from the at least one sinogram;
    determining the beam tracks of the metallic volume elements in an other of the at least one sinogram;
    determining a minimum measurement value of the detector signal data on each determined beam track of each metallic volume element respectively;
    substituting the deleted detector signal data by adding together the determined minimum measurement values of each of the beam tracks to obtain a calculated at least one sinogram; and
    using the calculated at least one sinogram to reconstruct computed tomography recordings of the patient without the metallic components.

2. The method as claimed in claim 1, wherein the method is used in conjunction with a volume reconstruction.

3. The method as claimed in claim 2, wherein the method is used in conjunction with spiral scanning.

4. The method as claimed in claim 2, wherein the method is used in conjunction with circular scanning.

5. The method as claimed in claim 1, wherein the method is used in conjunction with spiral scanning.

6. The method as claimed in claim 1, wherein the method is used in conjunction with circular scanning.

7. The method as claimed in claim 1, wherein a threshold value is set for the detector signal data to determine the detector signal data attenuated by the metallic components in the patient.

8. The method as claimed in claim 1, wherein, to determine the detector signal data attenuated by the metallic components in the patient, a backprojection is performed with the originally determined projection data followed by segmentation of the metallic components, with the detector signal data, which was attenuated by the metallic components in the patient, being determined in the at least one sinogram by way of geometric calculations.

9. The method as claimed in claim 1, wherein, to determine the detector signal data attenuated by the metallic components in the patient, a material decomposition is performed with the aid of at least two energy-specific items of image data to determine the metallic components, with the detector signal data, which was attenuated by the metallic components in the patient, being determined in the at least one sinogram by way of geometric calculations.

10. The method as claimed in claim 1, wherein the at least one sinogram is a parallel projection.

11. The method as claimed in claim 1, wherein the at least one sinogram is a conical projection.

12. The method as claimed in claim 1, wherein the calculated sinogram data of the at least one sinogram is smoothed.

13. The method as claimed in claim 12, wherein the smoothing of the calculated sinogram data also takes place at least in relation to measurement data already present.

14. The method as claimed in claim 13, wherein smoothing takes place by mean value formation in a boundary region between the calculated sinogram data and the at least one sinogram.

15. The method as claimed in claim 13, wherein smoothing takes place by adjusting a mean data value in the calculated sinogram data and a mean data value in adjacent data of the at least one sinogram.

16. The method as claimed in claim 13, wherein a weighted mean value between the calculated sinogram data and the at least one sinogram for reconstruction is used for smoothing purposes.

17. The method as claimed in claim 12, wherein smoothing takes place by mean value formation in a boundary region between the calculated sinogram data and the at least one sinogram.

18. The method as claimed in claim 12, wherein smoothing takes place by adjusting a mean data value in the calculated sinogram data and a mean data value in adjacent data of the at least one sinogram.

19. The method as claimed in claim 12, wherein a weighted mean value between the calculated sinogram data and the at least one sinogram for reconstruction is used for smoothing purposes.

20. The method as claimed in claim 1, wherein attenuation values are input in the reconstructed computed tomography recordings in a region of the metallic components.

21. The method as claimed in claim 20, wherein the attenuation values correspond to the attenuation values of metal.

22. A computer system for reconstruction, evaluation and display of CT image data, comprising:
- a program storage unit including computer programs, wherein at least one of the computer programs is configured to execute the method of claim 1 during operation of the computer system.

23. A computer readable medium including program segments for, when executed on a computer device, causing the computer device to implement the method of claim 1.

* * * * *